(12) United States Patent
Kuczynski

(10) Patent No.: US 8,551,101 B2
(45) Date of Patent: Oct. 8, 2013

(54) METHODS AND APPARATUS FOR PREPARING A PATIENT'S FEMUR FOR PATELLOFEMORAL KNEE ARTHROPLASTY

(75) Inventor: John Kuczynski, Clifton, NJ (US)

(73) Assignee: Arthrex, Inc., Naples, FL (US)

( * ) Notice: Subject to any disclaimer, the term of this patent is extended or adjusted under 35 U.S.C. 154(b) by 203 days.

(21) Appl. No.: 12/901,895

(22) Filed: Oct. 11, 2010

(65) Prior Publication Data

US 2012/0089147 A1    Apr. 12, 2012

(51) Int. Cl.
 *A61B 17/16* (2006.01)
 *A61B 17/17* (2006.01)
 *A61B 17/90* (2006.01)

(52) U.S. Cl.
 USPC ............. 606/88; 606/79; 606/84; 606/86 R; 606/96; 606/184

(58) Field of Classification Search
 USPC ............. 606/79, 84, 86 R, 87–89, 96, 184
 See application file for complete search history.

(56) References Cited

U.S. PATENT DOCUMENTS

| | | | |
|---|---|---|---|
| 4,474,177 A | 10/1984 | Whiteside | |
| 5,098,436 A * | 3/1992 | Ferrante et al. | 606/88 |
| 5,405,349 A | 4/1995 | Burkinshaw et al. | |
| 5,709,689 A | 1/1998 | Ferrante et al. | |
| 5,769,854 A | 6/1998 | Bastian et al. | |
| 5,916,221 A * | 6/1999 | Hodorek et al. | 606/88 |
| 2004/0153066 A1 | 8/2004 | Coon et al. | |

OTHER PUBLICATIONS

Extended European Search Report dated Jan. 9, 2012 for EP Application No. 11250841.1.
"Why precision is powerful", marketing material Smith & nephew, pp. 1-6 (2008).

* cited by examiner

*Primary Examiner* — Kevin T Truong
*Assistant Examiner* — Tracy Kamikawa
(74) *Attorney, Agent, or Firm* — Carlson, Gaskey & Olds, P.C.

(57) ABSTRACT

Methods and apparatus provide for modifying a patient's femur to receive a patellofemoral prosthesis, including: a distal punch, an anterior punch and a trochlear punch which are used in well defined orientations to remove material from the femur to accommodate complex geometries of a patellofemoral prosthesis; and optionally a guide operating to engage a distal end of the femur, the guide including a distal slot, an anterior slot and a transverse slot, which ensure that the punches achieve the desired orientations.

24 Claims, 9 Drawing Sheets

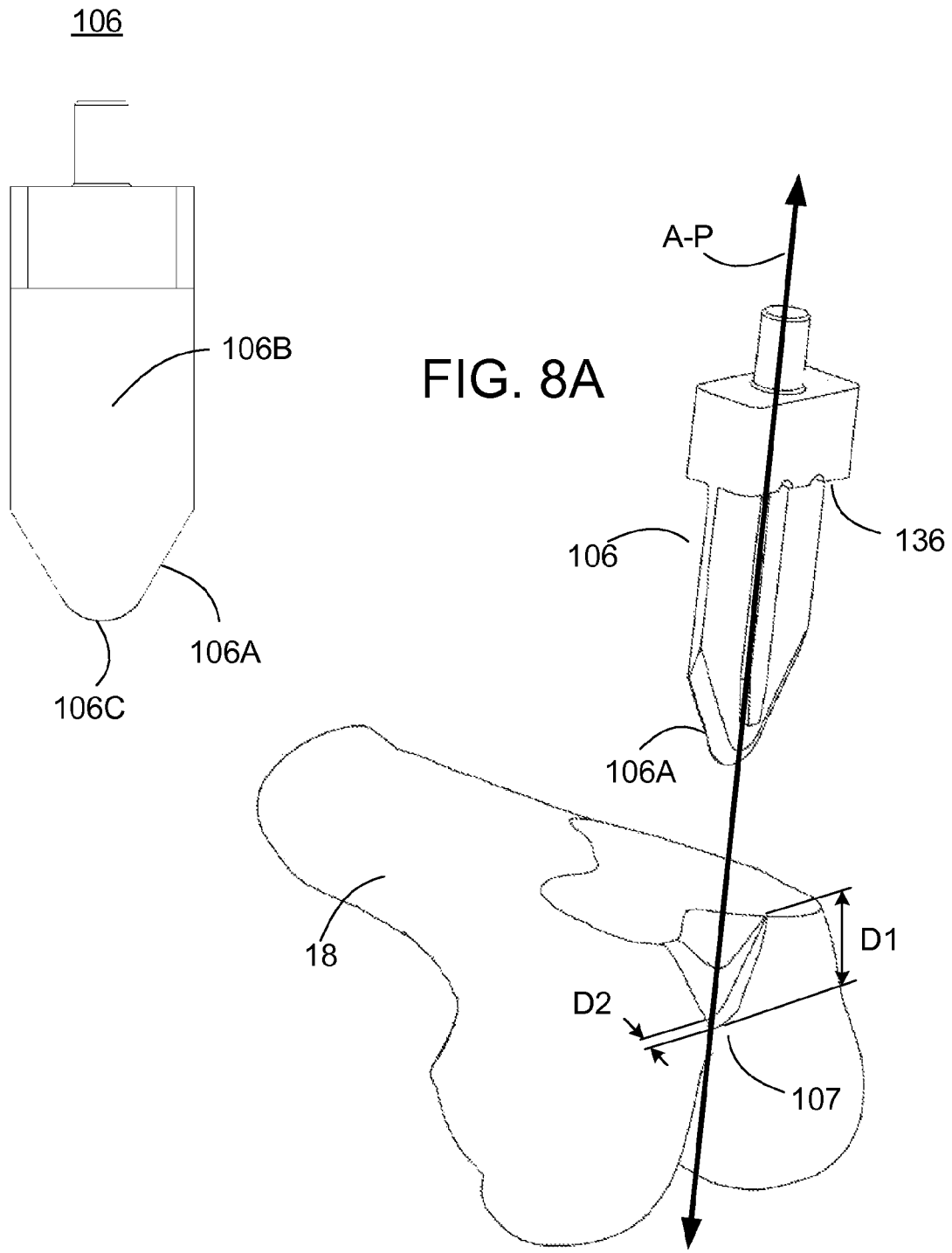

METHODS AND APPARATUS FOR PREPARING A PATIENT'S FEMUR FOR PATELLOFEMORAL KNEE ARTHROPLASTY

BACKGROUND OF THE INVENTION

The present invention relates to methods and apparatus for modifying a patient's femur in order to prepare same for receiving a patallofemoral knee arthroplasty.

The patellofemoral joint of the knee is an articulating joint between the patella and the femur. This joint includes an articular surface on the posterior of the patella and a corresponding articular surface on the anterior distal portion of the femur, also termed the trochlear groove. The posterior of the patella is contoured as a ridge, while the trochlea is contoured as a groove that is dimensioned to receive the patellar ridge in a complementary manner. Proper dynamic function of the patellofemoral joint requires that the patellar ridge accurately track the underlying trochlear groove when the knee is moved through flexion or extension.

Joint disorders arise with varying severity, pain and dysfunction. Some less severe, disorders involve minimal or no errors in patellar tracking of the trochlear groove. Other more serious disorders are characterized by patellar misalignment, transient displacement, or dislocation (such as permanent displacement, of the patella from the trochlear groove).

During functional movement of the knee joint, various tracking errors can occur due to injury, overuse, or changes inherent to adolescent growth, which in each case causes pain and dysfunction. When the patella is seated in the trochlear groove at a range greater than about 60 degrees of knee flexion, there is very little movement of the patella outside of the trochlear groove. Between about 0-40 degrees of knee flexion, and especially about 20-40 degrees, however, there is a propensity for the patella to track away from the groove as the knee flexes.

Rehabilitation of the weakened joint is often limited to the extent that correct tracking is absent, or ineffectively applied, and the resulting pain makes exercise too unbearable. As the quadriceps contract, they apply a lever force to the patellofemoral joint that is substantially directly related to the overall patellofemoral joint stress. Pain associated with such stress increases in relation to the amount of overall stress. Accordingly, as the quadriceps contract more powerfully, such as while going up stairs or doing squats, overall stress and associated pain increases.

In addition, patellofemoral joint stress at any given contact area increases as the overall patellofemoral joint stress is focused about a smaller patellofemoral contact surface area. Pain associated with such stress increases in direct relation to a reduction in the amount of patella-to-femur contact surface area. Thus, patellofemoral pain is not only directly related to the overall joint force applied between the patella and the femur, it is inversely related to the amount of patellofemoral contact surface area. Rehabilitation of the weakened joint through quadriceps contraction is therefore limited by the pain associated with both overall patellofemoral joint stress and a minimal patellofemoral contact surface area.

Joint arthroplasty is a surgical procedure by which a diseased and/or damaged natural joint is replaced by a prosthetic joint. Patellofemoral arthroplasty is a type of joint arthroplasty wherein the anterior compartment of a patient's knee, or portion thereof, is replaced with one or more prosthetic components. Additionally, in some cases, the patient's patella may be replaced by an orthopedic prosthesis. Typical patellofemoral arthroplasty procedures may include replacing a patient's femoral trochlea, and in some cases, one or both femoral condyles with prosthetic components. Typical orthopedic surgical procedures require the entire anterior femur to be resectioned to allow overlay of the prosthetic joint components. However, the prosthetic joint components may not replace the entire volume of resectioned bone. Additionally, many patellofemoral arthroplasty procedures and instrumentation reference off of the intramedullary canal of the patient's femur, which resultantly compromises the intramedullary canal.

Different methods and apparatus have been developed in the past to enable a surgeon to remove bony material to create specifically shaped surfaces in or on a bone for various reasons, including to allow for attachment of various devices or objects to the bone. Keeping in mind that the ultimate goal of any surgical procedure is to restore the body to normal function, it is important that the quality and orientation of the cut, as well as the quality of fixation, and the location of the component(s) of the prosthesis are all sufficient. It has been said that a "well placed, but poorly designed implant will perform well clinically, while a poorly placed, well designed implant will perform poorly clinically."

Unfortunately, the conventional methods and apparatus for preparing the femur for a patellofemoral prosthesis result too often in misalignments and/or poor fit between the prepared anterior and distal portions of the femur and the prosthesis. Clinical results, therefore, suffer.

In view of the above, there are needs in the art for new methods and apparatus for preparing a patient's femur in order to receive a patellofemoral knee prosthesis. Among the desired characteristics of such new methods and apparatus are the ability to yield a modified anterior and/or distal femur that exhibits tightly controlled cuts in order to achieve repeatable, accurate, and precise alignment and fit of the prosthesis to the femur.

SUMMARY OF THE INVENTION

In accordance with one or more aspects of the present invention, an apparatus for modifying a patient's femur for receiving a patellofemoral prosthesis, includes: a guide operating to engage a distal end of the femur, the guide including a mounting element disposed at a first end of the guide, having an engagement surface defining an anterior resection plane, and operating to rigidly couple the guide to an anterior resection surface of the femur. The guide also includes a distal stop element extending from a second, opposite end of the guide, and operating to engage a surface of the patellar groove of the femur. This establishes a repeatable, accurate, and precise position at which the mounting element is coupled to the anterior resection surface of the femur.

The guide further includes: (i) a transverse slot extending through the guide in a transverse direction, which is substantially transverse to: the anterior resection plane, a distal-proximal direction, and the anterior-posterior direction, (ii) a distal slot extending through the guide, substantially parallel to the anterior resection plane, toward the patellar groove in the distal-proximal direction, and (iii) an anterior slot extending through the guide, substantially transverse to the anterior resection plane, toward the patellar groove in an anterior-posterior direction when the guide is coupled to the femur.

The system further includes a distal punch having a cutting edge and being sized and shaped to slidingly pass through the distal slot such that the cutting edge penetrates into the patellar groove of the femur, in the distal-proximal direction, producing a distal cut. The system further includes an anterior punch having a cutting edge and being sized and shaped to slidingly pass through the anterior slot such that the cutting edge penetrates into the patellar groove of the femur, in the anterior-posterior direction, producing an anterior cut. The system also includes a trochlear punch having a cutting edge and being sized and shaped to slidingly pass through the transverse slot such that the cutting edge penetrates through the anterior resection surface and through the anterior cut, thereby forming a trochlear cut in both anterior and distal portions of the femur.

The respective cutting edges of the distal punch, the anterior punch, and the transverse punch, as well as the orientations of the respective distal, anterior, and transverse slots, are sized and shaped such that the anterior cut meets the distal cut, and the trochlear cut meets the anterior cut, such that a portion of the patient's femur is removed to receive the patellofemoral prosthesis.

Other aspects, features, and advantages of the present invention will be apparent to one skilled in the art from the description herein taken in conjunction with the accompanying drawings.

DESCRIPTION OF THE DRAWINGS

For the purposes of illustration, there are forms shown in the drawings that are presently preferred, it being understood, however, that the invention is not limited to the precise arrangements and instrumentalities shown.

FIGS. 8A and 8B are a respective perspective view of an anterior punch referenced to the patient's femur, and a side (rear) view of the punch, which punch may be utilized with the system of FIG. 5.

DETAILED DESCRIPTION OF THE PREFERRED EMBODIMENTS

Figure 1:
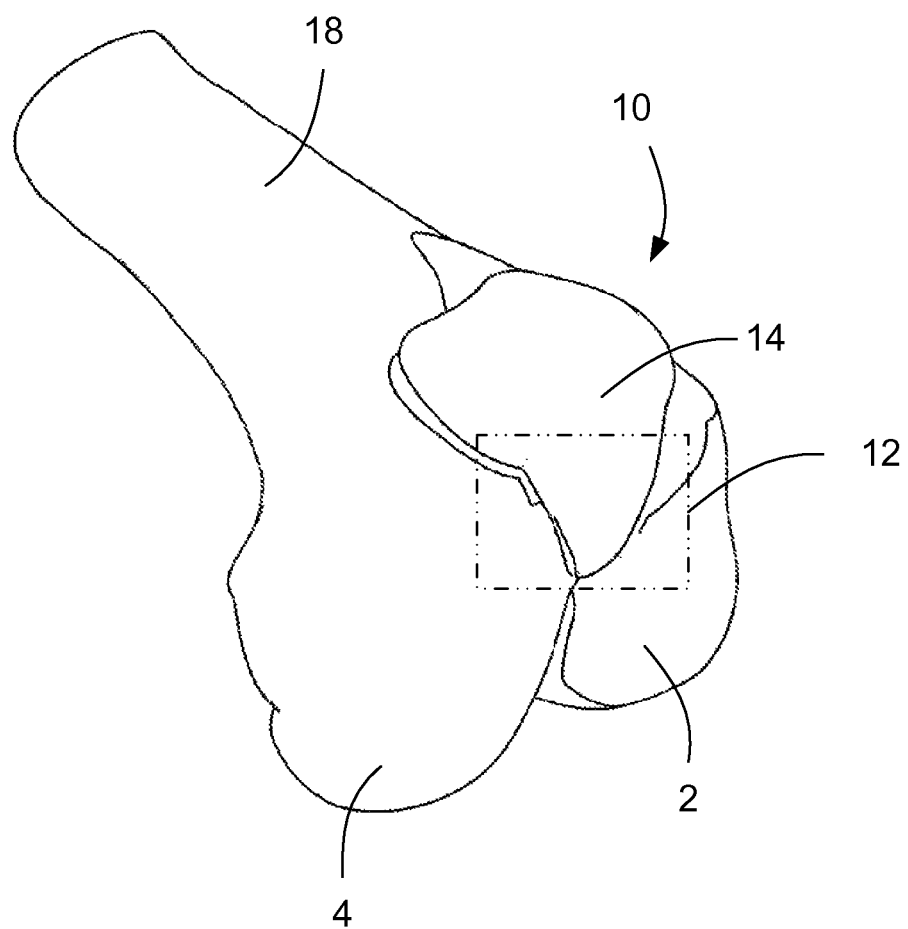
FIG. 1 is perspective view of a patellofemoral knee prosthesis connected to a femur of a patient in accordance with one or more aspects of the present invention.
Figure 2A:
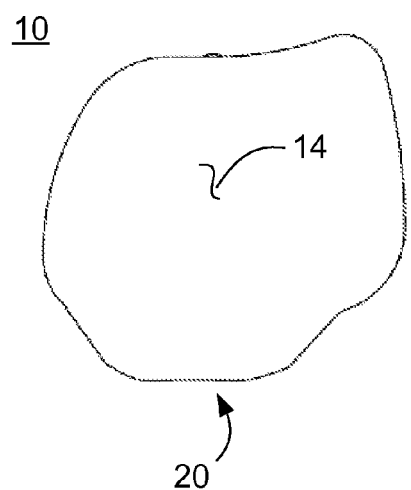
FIGS. 2A, 2B, 2C, and 2D illustrate front, bottom, rear and side views of the prosthesis of FIG. 1.
Figure 2B:
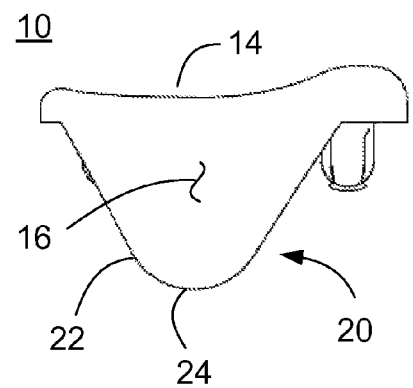
Figure 2C:
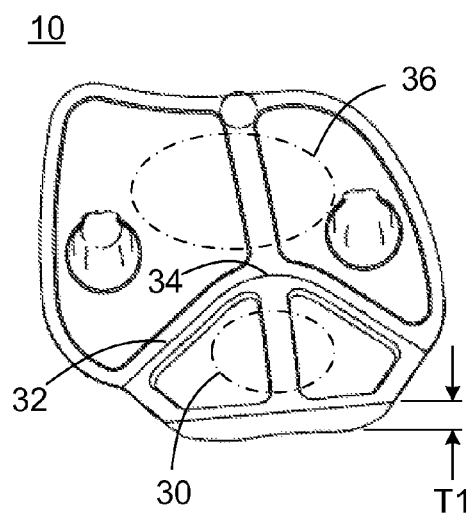
Figure 2D:
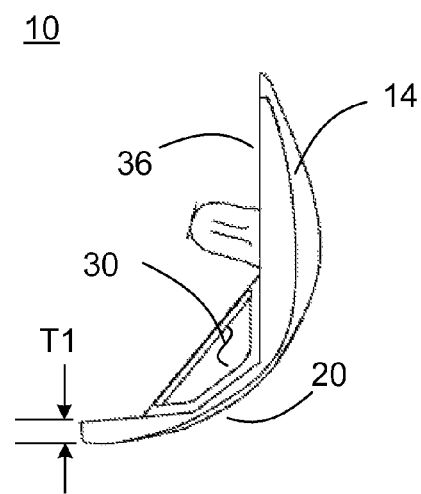

With reference to the drawings, wherein like numerals indicate like elements, a patellofemoral knee prosthesis 10 is shown in FIG. 1 connected to a right femur 18 of a patient. The femur 18 is shown stripped of all other anatomical structures normally present for purposes of clarity. The femur 18 includes a medial condyle 2, a lateral condyle 4, and the prosthesis 10 disposed in the intercondylar area of the anterior and distal portions of the femur 18. As will be discussed in more detail below, the methods and apparatus disclosed and described herein are directed to achieving a modified anterior and/or distal femur 18 that exhibits tightly controlled cuts in order to achieve repeatable, accurate, and precise alignment and fit of the prosthesis 10 to the femur 18, especially in the area circumscribed by, and/or near, the dotted line 12.

FIGS. 2A, 2B, 2C, and 2D illustrate front, bottom, rear and side views of the prosthesis 10 and certain structural details thereof, which should be considered in preparing the femur 18 for receiving the prosthesis 10. The prosthesis 10 includes a surface 14 that is sized and shaped to mimic the contours of a healthy trochlear groove of the femur 18. The surface 14 extends over an anterior region of the femur 18 and then transitions to a distal surface 16 that extends towards, and into, an intercondylar region of the femur 18, between the medial condyle 2 and the lateral condyle 4. The distal surface is generally concave to mimic the contours of a healthy distal and intercondylar notch area of the femur 18. The distal surface 16 is an element of a distal member 20, having a generally V-shaped peripheral edge 22 (which may include a rounded inflection region 24). The distal member 20 also includes a thickness, T1, which is determined by the requisite strength, the material properties of the prosthesis 10, and other factors of mechanical design. The distal member 20 also includes a convex rear surface 30, of generally complementary shape to the concave shape of the distal surface 16 (on the opposite side of the distal member 20. An edge 32 extends along a transitional region between the convex rear surface 30 and a further rear surface 36 (opposite the surface 14) of the prosthesis 10. The transitional edge 32 is of a compound V-shape, including a rounded inflection region 34.

Most, if not all, aspects of the preparation and modification of the femur 18 are important in achieving clinical success with the prosthesis 10. Without significant attention to the preparation of the anterior and distal portions of the femur 18 to receive the distal member 20 (such as the thickness T1, the shape and contour of the surface 30, the shapes of the edges 22, 32, etc.), however, a poor fit may result. To accommodate such complex geometries, and without proper methods and tools, surgeons are likely to either spend significant time during preparation of the femur 18, or improperly modify the femur 18. Various aspects and embodiments of the present invention address such femur preparation issues.

Figure 3:
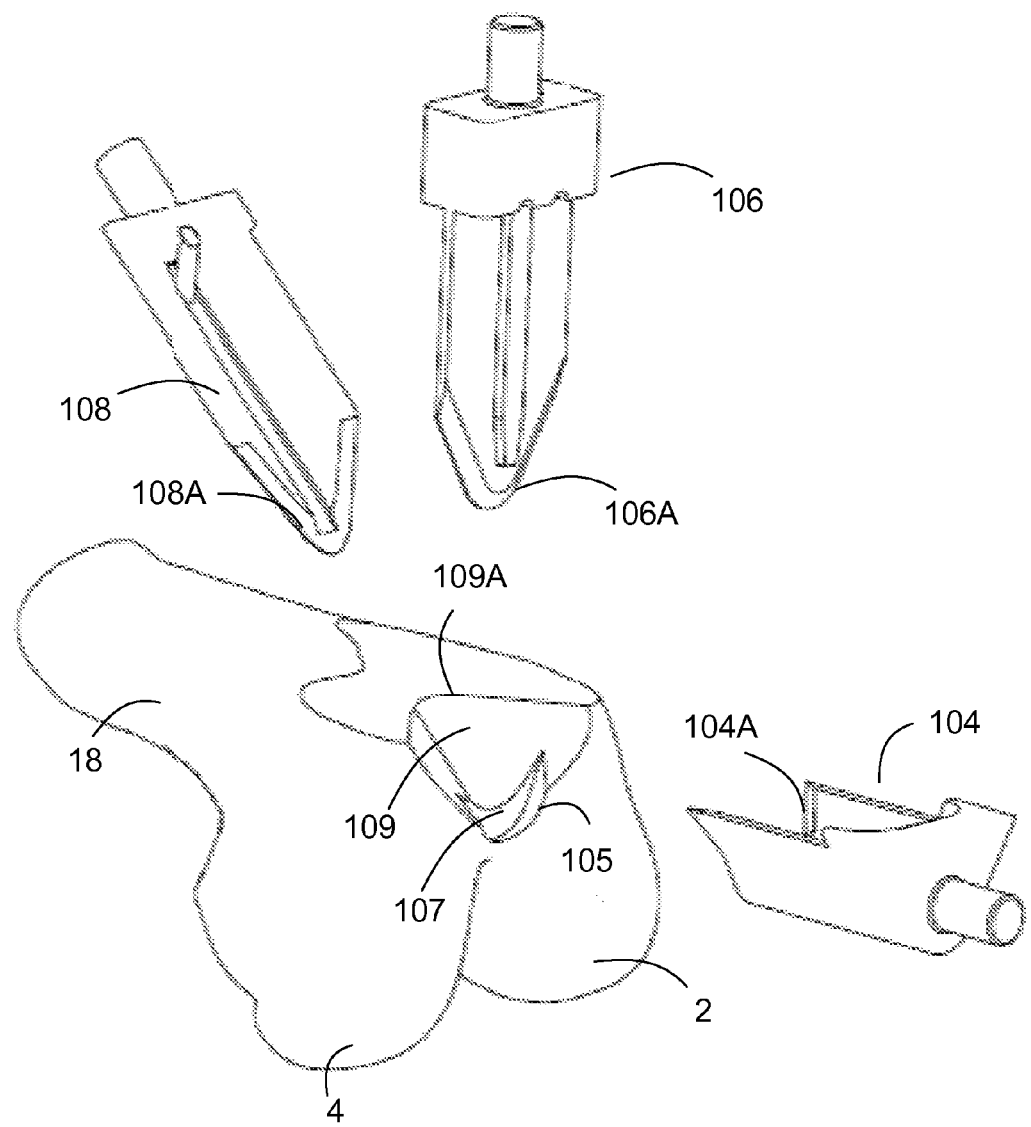
FIG. 3 is a distal perspective view of a system for modifying the anterior and distal portions of the femur to accommodate a patellofemoral knee prosthesis.

With reference to FIG. 3, a system 100A is employed to modify the anterior and distal portions of the femur 18 to accommodate the complex geometries of the prosthesis 10. The system includes a plurality of punches 104, 106, 108. The system 100A is intended to apply well defined orientations for punches 104, 106, 108 to remove material from the femur 18 to accommodate, for example, the distal member 20 of the prosthesis 10. The punches 104, 106, 108 are specifically designed to ensure that the anterior and distal portions of the femur 18 are properly modified to receive the distal member 20 (such as the thickness T1, the shape and contour of the surface 30, the shapes of the edges 22, 32, etc.).

The distal punch 104 includes a cutting edge 104A that is sized and shaped to penetrate into the patellar groove of the femur 18 in a distal-proximal direction, producing a distal cut 105. The anterior punch 106 includes a cutting edge 106A that is sized and shaped to penetrate into the patellar groove of the femur 18 in an anterior-posterior direction, producing an anterior cut 107. The trochlear punch 108 includes a cutting edge 108A that is sized and shaped to penetrate through an anterior portion of the femur 18 and through the anterior cut, thereby forming a trochlear cut 109 in both anterior and distal portions of the femur 18.

A depth of the distal cut 105 is important, and thus, a distance through which the punch 104 slides is preferably limited by way of the surgeon's skill or otherwise to ensure that the cutting edge 104A of the distal punch 104 may extend only a predetermined distance into the femur 18 in the distal-proximal direction, thereby defining the depth of the distal cut 105. The cutting edge 104A of the distal punch 104 defines a V-shaped edge (and thus a V-shaped distal cut 105), when viewed in the distal-proximal direction. It is noted that the V-shaped edge and cut 105 are sized and shaped to complement the shape and contour of the distal member 20 of the prosthesis 10, specifically the a generally V-shaped peripheral edge 22 (which also may include the rounded inflection region 24).

As will be discussed in more detail below, there are two depths of the anterior cut 107 that are important. The first is an anterior-posterior depth, and the second is a distal-proximal depth. When the aforementioned depths are properly made, the anterior cut 107 meets the distal cut 105 at precisely the right places to cause a piece of the distal femur to be removed, thereby leaving a cavity that may at least partially receive the distal portion 20 of the prosthesis 10. The cutting edge 106A of the distal punch 104 defines a V-shaped edge (and thus a V-shaped anterior cut 107), when viewed in the distal-proximal direction. It is noted that the V-shaped edge and cut 106 are again sized and shaped to complement the shape and contour of the distal member 20 of the prosthesis 10, specifically the a generally V-shaped peripheral edge 22 (which also may include the rounded inflection region 24).

The trochlear cut 109 is of generally concave cross-section (or grooved as the name implies) in order to complement the convex rear surface 30 of the distal member 20 of the prosthesis 10. A most proximal edge 109A of the trochlear cut 109 complements the edge 32 of the prosthesis 10 that extends along a transitional region between the convex rear surface 30 and the further rear surface 36 (opposite the surface 14) of the prosthesis 10. Thus, both the proximal edge 109A and the transitional edge 32 are of compound V-shape, including matching rounded inflection regions. As one skilled in the art will appreciate from the discussion herein, a depth (compound depth from the anterior and distal directions) and orientation of the trochlear cut 109 are important in order to ensure that the prosthesis 10 fits properly into the cavity thereby formed in the femur 18.

Figure 4:
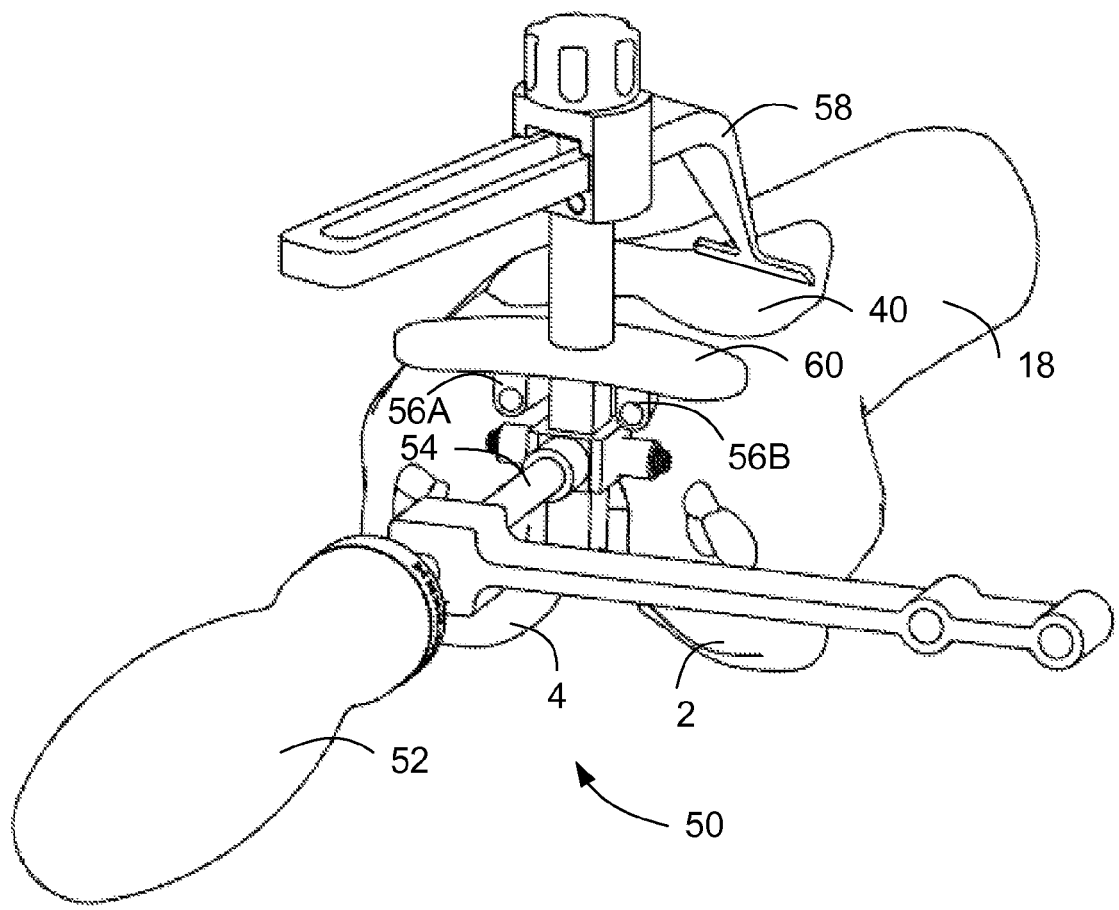
FIG. 4 is a distal perspective view of a tool for resection of an anterior portion of the patient's femur to accommodate further apparatus and methods in accordance with one or more further aspects of the present invention.

In accordance with one or more embodiments, and with reference to FIG. 4, the distal femur 18 of the patient is prepared before applying the punches 104, 106, 108 to the femur 18. In particular, the femur 18 is prepared by forming at least one resection, specifically an anterior resection, to create an anterior resection surface 40. It is understood that while it may be desirable to perform a resection 40, such is not required in all embodiments of the invention. For purposes of discussion, however, producing a resection surface 40 on the femur 18 will be considered in some detail. A number of known surgical procedures are available to surgeons that will enable them to produce the aforementioned resection. Various knee prosthesis manufacturers publish procedures for use by surgeons in implanting their prostheses, such as by Howmedica, Inc. and Zimmer USA, Inc. For the purposes of discussion, acceptable surgical procedures to create the resections may be found in any number of publications, such as U.S. Pat. No. 4,474,177, which is hereby incorporated herein in its entirety. It is understood, however, that the particular procedure for producing the resections is not intended to limit the scope of the inventive embodiments herein.

With reference to FIG. 4, suitable methods and apparatus for producing the anterior resection surface 40 will now be described. The technique involves the use of a resection tool 50, which includes a handle 52, a shaft 54, a mounting plate, a stylus 58, and a cutting guide 60. A point of the tool 50 is placed at a center of the femur 18. The external rotation is determined by referencing the Whiteside's line, with a secondary reference to the medial and lateral condyles 2, 4. The Q-Angle is aligned using the long shaft 54 of the handle 52 as a reference, when viewed from a sagittal point of view. Alignment may also be evaluated and established using extramedullary rods if desired. The tool 50 is pinned into place via the mounting plate, which includes mounting holes 56A, 56B. The resection guide 60 is used to establish a reference surface for a saw to remove the bone, cartilage, etc., and the resection depth is determined using the anterior stylus 58. The femur 18 of the patient is thus modified to include an anterior resection, creating the anterior resection surface 40.

Figure 5:
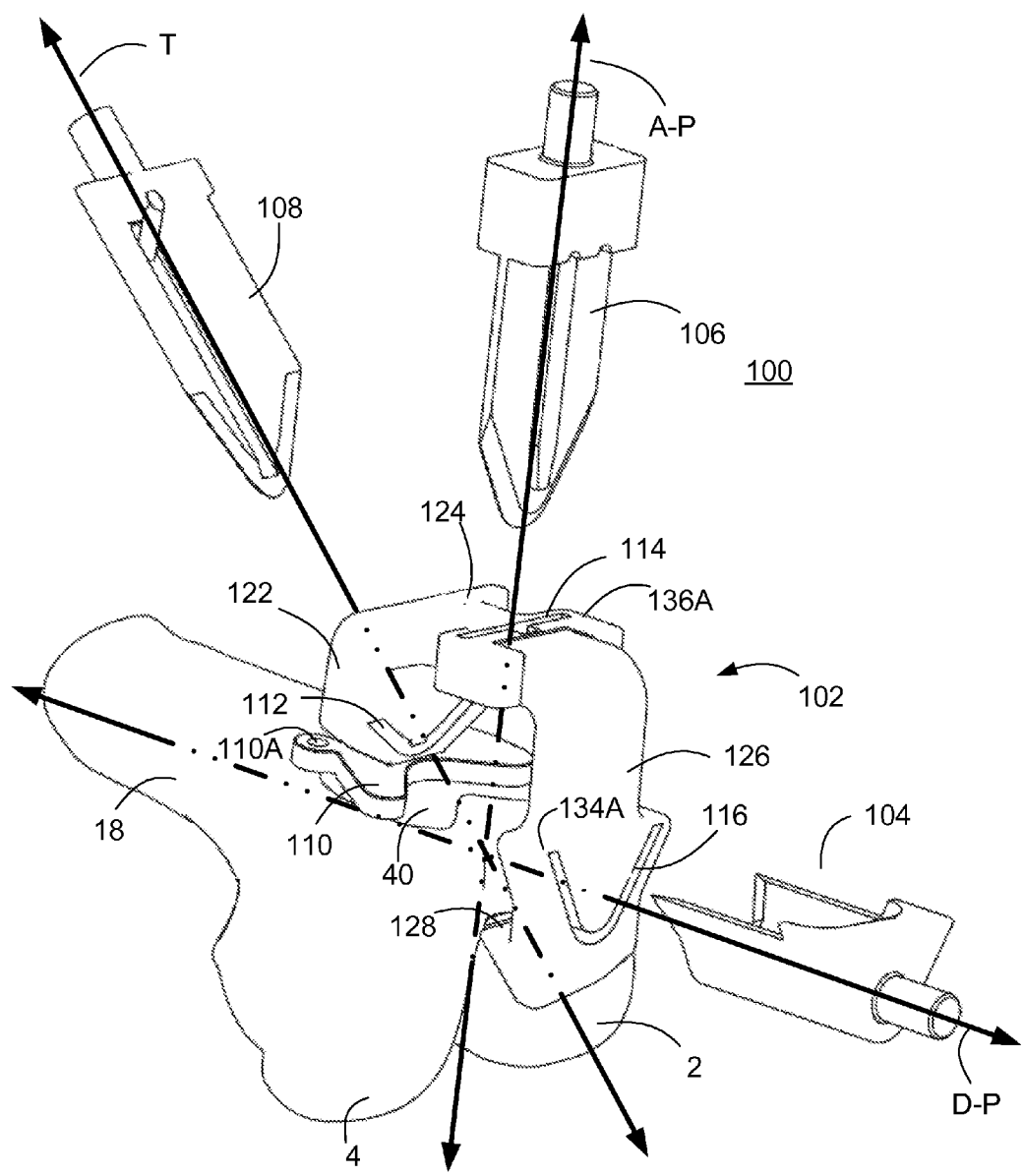
FIG. 5 is a distal perspective view of an alternative, preferred system for modifying the anterior and distal portions of the femur to accommodate a patellofemoral knee prosthesis.
Figure 6A:
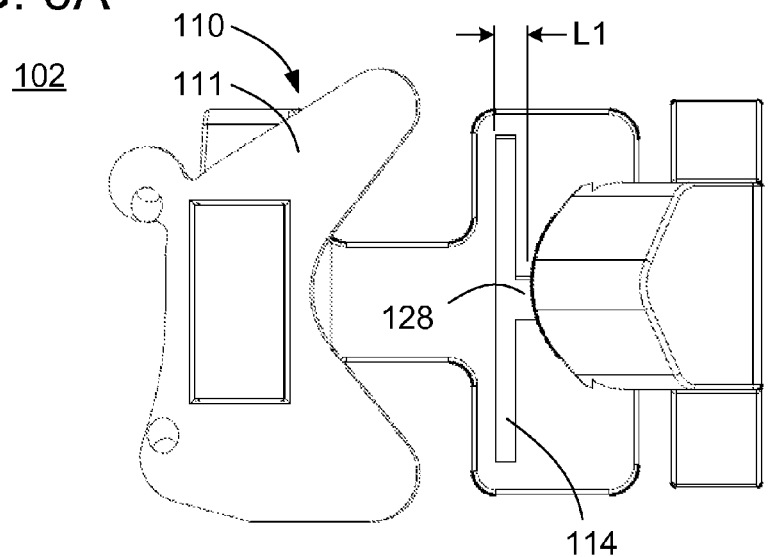
FIGS. 6A and 6B are respective bottom and side views of a guide of the system of FIG. 5.
Figure 6B:
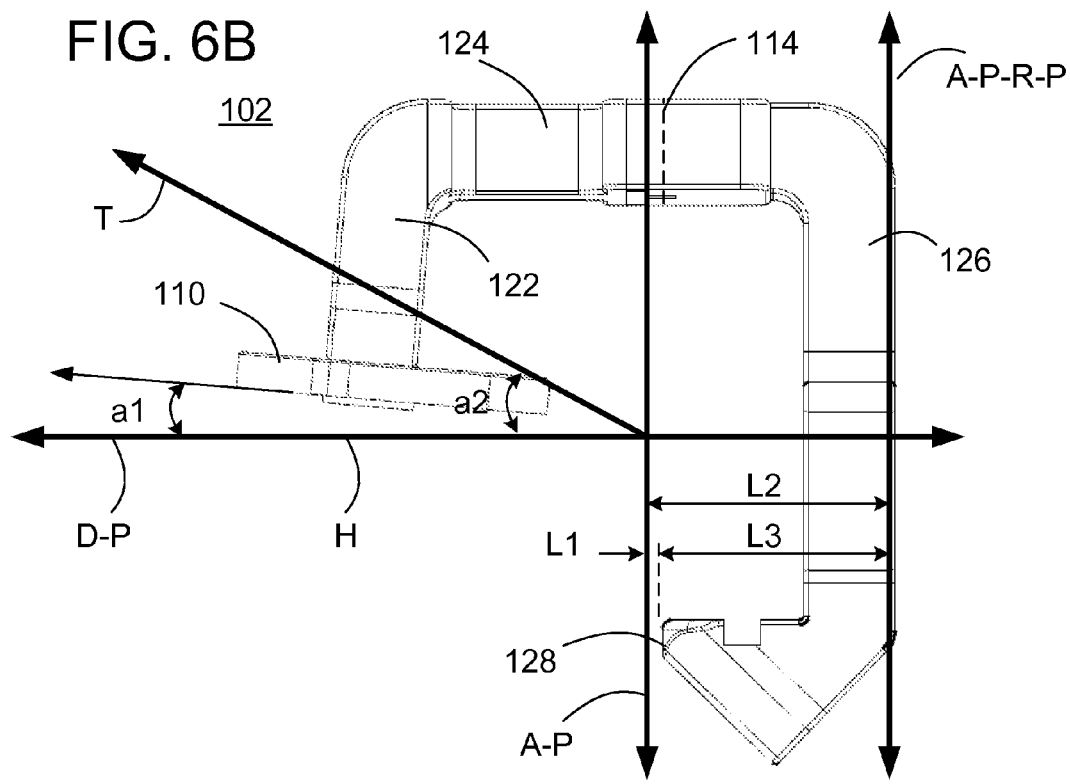

With reference to FIGS. 5 and 6A-6B, an alternative system 100 is employed to modify the anterior and distal portions of the femur 18 to accommodate the complex geometries of the prosthesis 10. The system includes a guide 102 and a plurality of punches 104, 106, 108. The guide 102 is sized and shaped to firmly engage the distal end of the patient's femur 18 and to provide well defined orientations of respective slots for the punches 104, 106, 108. Such functionality of the guide 102 ensures that the punches 104, 106, 108 remove material from the femur 18 to accommodate, for example, the distal member 20 of the prosthesis 10. The guide 102 and punches 104, 106, 108 are specifically designed to ensure that the anterior and distal portions of the femur 18 are properly modified to receive the distal member 20 (such as the thickness T1, the shape and contour of the surface 30, the shapes of the edges 22, 32, etc.).

The guide 102 includes a mounting element 110 disposed at a first end of the guide 102, which operates to rigidly couple the guide 102 to the anterior resection surface 40 of the femur 18. Again, it is understood that an anterior resection surface 40 is not required to use the guide 102, as the mounting element 110 (and/or other mounting elements not shown) may be designed to engage the existing anatomical structure(s) of an unmodified femur 18. For purposes of discussion, however, the anterior resection surface 40 is assumed to exist for this embodiment.

As best seen in FIG. 6A, which is a bottom view of the guide 102, the mounting element 110 includes an engagement surface 111 (defining an anterior resection plane), which is coupled to, and coplanar with, the anterior resection surface 40 when the guide 102 is mounted to the femur 18. The guide 102 may be secured to the femur 18 by way of one or more mounting apertures 110A in the mounting plate 110, which apertures 110A are positioned such that corresponding fixation pins (threaded or otherwise) may be inserted through the apertures 110A and fix the guide 102 to the distal femur 18. Any of the known and readily available fixation pins may be employed for this purpose.

The guide 102 may include one or more of: a transverse slot 112, an anterior slot 114, and a distal slot 116, extending therethrough, where each such slot is sized and shaped to slidingly receive a respective one of the punches 104 (a distal punch), 106 (an anterior punch), and 108 (transverse punch 108). The orientations, sizes and shapes of the slots 112, 114, and/or 116, as well as the sizes and shapes of the transverse, anterior and distal punches 108, 106, 104 are such that the respective punches may be driven through the respective slots and into the femur 18, thereby removing pieces of material and leaving suitable cavities, contours, and peripheral edge characteristics to receive the prosthesis 10.

The distal slot 116 extends through the guide 102, substantially parallel to the anterior resection plane (which one may envision is co-planar with the anterior resection surface 40), toward the patellar groove in a distal-proximal direction (see axis D-P) when the guide 102 is coupled to the femur 18. The anterior slot 114 extends through the guide 102 substantially transverse to the anterior resection plane, toward the patellar groove in an anterior-posterior direction (see axis A-P) when the guide 102 is coupled to the femur 18. The transverse slot 112 extends through the guide 102 in a transverse direction (see axis T), which is substantially transverse to at least one, and preferably all, of: (i) the anterior resection plane, (ii) the distal-proximal direction D-P, and (iii) the anterior-posterior direction A-P. In accordance with one or more embodiments, the anterior-posterior direction A-P and the distal-proximal direction D-P are preferably orthogonal to one another.

For purposes of discussion, the distal slot 116 is described as extending through the guide 102, substantially parallel to the anterior resection plane (anterior resection surface 40). Such orientation of the distal slot 116, however, may be referenced to one or more other anatomical reference plane(s) and/or axes of the patient. Such anatomical reference plane(s) may be one or more of a sagittal plane, a coronal plane, and/or a transverse plane of the patient.

While the slots 112, 114, and 116 may be considered to extend through the guide 102, the guide 102 may considered to include a frame, where the frame includes a proximal section 122, an anterior section 124, and a distal section 126.

The proximal section 122 extends away from the mounting element 110 of the guide 102 along an axis substantially parallel to the anterior-posterior direction A-P. As best seen in FIG. 6B, and depending on the specific or general anatomical geometries of the femur 18, the proximal section 122 may be oriented such that the axis thereof extends slightly transverse to the anterior-posterior direction A-P, such as at an acute angle, a1, of about 2-8°, about 4-6°, and/or about 5°. This orientation may place the mounting plate 110 at a similar angle with respect to a horizontal reference plane H (which is shown in FIG. 6B to be co-planar with the axis D-P).

The transverse slot 112 extends through the proximal section 122 of the frame, in the transverse direction T. The transverse direction T extends at an acute angle, a2, of about 15-45°, preferably about 30°, with respect to at least one of: the anterior resection plane (coplanar with the anterior resection surface 40), the distal-proximal direction D-P, and/or the horizontal plane H. Again, for purposes of discussion, the transverse slot 112 has been described as extending through the proximal section 122 of the guide 102, in the transverse direction T, where the direction T is referenced to any number of planes/axes. In addition to those discussed above (i.e., the anterior resection plane, the anterior resection surface 40, the distal-proximal direction D-P, and/or the horizontal plane H), the direction T may be referenced to any one or more of the sagittal plane, the coronal plane, and/or the transverse plane of the patient.

The anterior section 124 extends away from the proximal section 122 of the guide 102, along an axis substantially parallel to the distal-proximal direction D-P, the horizontal plane H, and/or the anterior resection plane. The anterior slot 114 extends through the anterior section 124 of the frame, substantially transverse to the anterior resection plane, toward the patellar groove in the anterior-posterior direction A-P. It is understood that the anterior slot 114 may alternatively be referenced to one or more other anatomical references, such as the sagittal plane, the coronal plane, and/or the transverse plane of the patient.

The distal section 126 extends transversely away from the anterior section 124 along an axis substantially parallel to the anterior-posterior direction A-P, and/or substantially orthogonally with respect to the horizontal plane H and/or the anterior resection plane. The distal slot 116 extends through the distal section 126 of the frame, substantially parallel to the distal-posterior direction D-P and/or the anterior resection plane. Again, it is understood that the distal slot 116 may alternatively be referenced to one or more other anatomical references, such as the sagittal plane, the coronal plane, and/or the transverse plane of the patient.

In general, the proximal and distal sections 122, 126 of the frame extend substantially parallel to one another, while the anterior section 124 of the frame extends transversely with respect to both the proximal and distal sections 122, 126 of the frame. Of course, when the anterior resection surface 40 (and the plane thereof) is at the acute angle, a1, with respect to the horizontal plane H, it is possible that the proximal and distal sections 122, 126 of the frame extend slightly transverse (about 2-8°, 4-6°, and/or about 5°) with respect to one another, but generally parallel to one another. It is preferred that at least two of the proximal, anterior and distal sections 122, 124, 126 of the frame extend orthogonally with respect to one another, particularly the anterior and distal sections 124, 126. So long as the desired orientations of the slots 112, 114, and 116 are maintained with respect to the anterior resection surface 40 (and other anatomical structures of the femur 18), however, one skilled in the art will appreciate that the proximal, anterior, and distal sections 122, 124, and 126 of the frame extend (to one extent or another) transversely or orthogonally with respect to one another.

Since the desired orientations of the slots 112, 114, and 116 with respect to the femur 18 are highly dependent on exactly where the guide 102 is coupled to the femur 18, i.e., where the guide 102 is coupled to the anterior resection surface 40, the guide 102 includes a locating feature. In particular, the guide 102 includes a distal stop element 128 extending from a second, opposite end of the guide 102 (preferably the distal section 126 of the frame). The distal stop element 128 operates to engage a surface of the patellar groove of the femur 18. In a preferred configuration, the distal stop element 128 extends from the distal section 126 of the frame along an axis substantially parallel to the distal-proximal direction D-P, toward the patellar groove of the femur 18. As best seen in FIG. 6A, the distal stop element 128 includes a terminal end of arcuate (or curved) periphery, which preferably complements the concavity of the patellar groove in the distal area of the femur 18. When the guide 102 is placed onto the anterior resection surface 40 and slid in the distal-proximal direction D-P until the terminal end (specifically, the arcuate peripheral edge) engages the surface of the patellar groove, then the desired position at which the mounting element 110 is coupled to the anterior resection surface 40 of the femur 18 is established, and the orientations of the transverse, anterior, and distal slots 112, 114, 116 with respect to the femur 18 are also established.

Figure 7B:
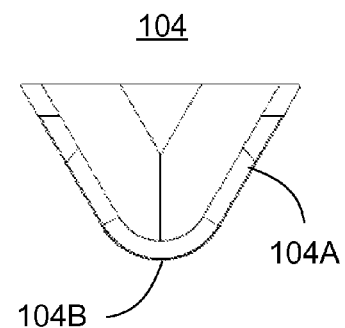
FIGS. 7A and 7B are a respective perspective view of a distal punch referenced to the patient's femur, and an end view of the punch, which punch may be utilized with the system of FIG. 5.
Figure 7A:
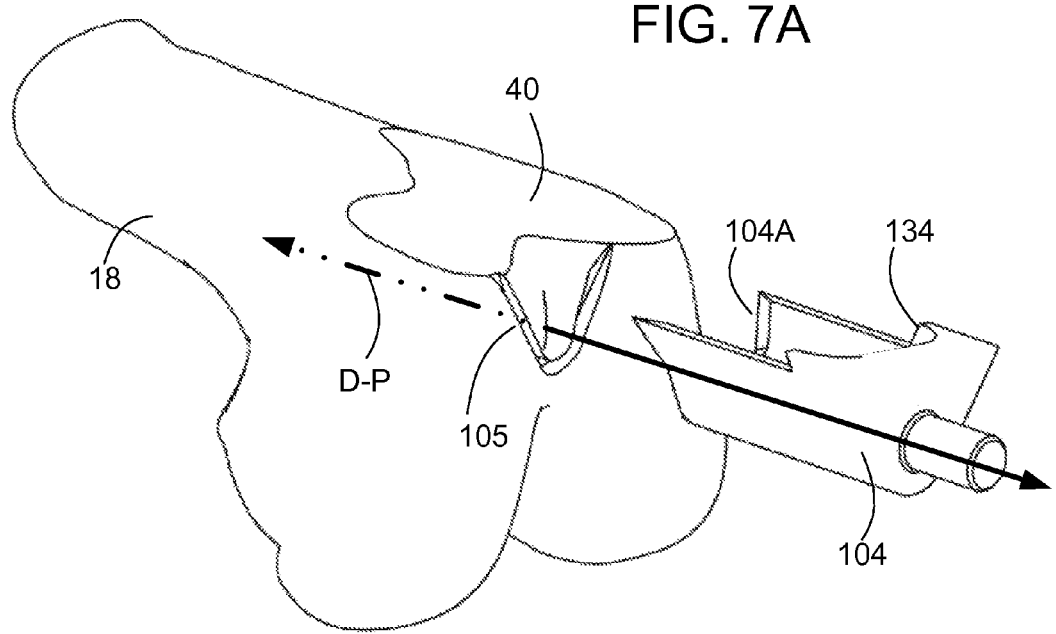

With reference to FIGS. 5 and 7A-7B, the distal punch 104 includes a cutting edge 104A, and is sized and shaped to slidingly pass through the distal slot 116, such that the cutting edge 104A penetrates into the patellar groove of the distal portion of the femur 18, in the distal-proximal direction D-P, producing a distal cut 105. A depth of the distal cut 105 is important, and thus, at least one of the distal punch 104 and the guide 102 (or frame thereof) includes a depth limiting element operating to limit the sliding of the distal punch 104 through the distal slot 116. By way of example, the punch 104 may include a collar 134 located proximate to a hub of the punch (which is the transition to a handle thereof, not shown). The collar 134 operates to engage a stop member 134A located at a periphery of the slot 116. In such a configuration, a distance through which the punch 104 slides through the slot 116 is limited. Such limiting ensures that the cutting edge 104A of the distal punch 104 may extend only a predetermined length past the distal stop 128, in the distal-proximal direction D-P, thereby defining the depth of the distal cut 105. Although aspects of the invention are not limited by any particular theory of operation, it has been found that desirable characteristics of the modified femur 18 are achieved when the depth of the distal cut 105 is in the range of about 1.0 to 8.0 mm.

The cutting edge 104A of the distal punch 104 defines a V-shaped edge (and thus a V-shaped distal cut 105), when viewed in the distal-proximal direction D-P. Preferably, the V-shaped edge includes a rounded inflection region 104B. It is noted that the V-shaped edge and cut 105 are sized and shaped to complement the shape and contour of the distal member 20 of the prosthesis 10, specifically the a generally V-shaped peripheral edge 22 (which also may include the rounded inflection region 24). However, at this point, with only the distal cut 105 having been made, the modifications to the distal femur 18 have not yet resulted in a cavity into which the distal portion 20 of the prosthesis 10 may be received.

With reference to FIGS. 5 and 8A-8B, the anterior punch 106 includes a cutting edge 106A, and is sized and shaped to slidingly pass through the anterior slot 114, such that the cutting edge 106A penetrates into the patellar groove of the distal portion of the femur 18, in the anterior-posterior direction A-P, producing an anterior cut 107.

There are two depths of the anterior cut 107 that are important. The first is the anterior-posterior depth D1, and the second is the distal-proximal depth D2. When the aforementioned depths D1 and D2 are properly made, the anterior cut 107 meets the distal cut 105 at precisely the right places to cause a piece of the distal femur 18 to be removed, thereby leaving a cavity that may at least partially receive the distal portion 20 of the prosthesis 10.

As to the anterior-posterior depth of cut D1, at least one of the anterior punch 106 and the guide 102 (or frame thereof) includes a depth limiting element operating to limit the sliding of the anterior punch 106 through the anterior slot 114. By way of example, the punch 106 may include a collar 136 located proximate to a hub of the punch (which is the transition to a handle thereof, not shown). The collar 136 operates to engage a stop member 136A located at a periphery of the slot 114. In such a configuration, a distance through which the punch 106 slides through the slot 114 is limited. Such limiting ensures that the cutting edge 106A of the anterior punch 106 may extend only a predetermined length (corresponding to depth of cut D1) into the distal femur 18, in the anterior-posterior direction A-P, thereby defining the anterior-posterior depth of cut D1 of the anterior cut 107. Although aspects of the invention are not limited by any particular theory of operation, it has been found that desirable characteristics of the modified femur 18 are achieved when the anterior-posterior depth of cut D1 of the anterior cut 107 is in the range of about 1.0 to about 8.0 mm.

As to the distal-proximal depth of cut D2, the guide 102 and the anterior punch 106 are designed such that the distal-proximal depth of cut D2 corresponds repeatably, accurately, and precisely with the thickness T1 of the distal portion 20 of the prosthesis 10. With reference to FIGS. 6A and 6B, this is achieved by placing the anterior slot 114 and the distal stop element 128 in desirable positions with respect to one another along the distal-proximal direction D-P. As seen in FIG. 6A, the slot 114 (and specifically a most proximal interior surface thereof that engages a rear surface 106B of the punch 106) is placed a distance L1 from the terminal end of the distal stop element 128 along an axis (or respective axes) parallel to the distal-proximal direction D-P. The distance L1 establishes the distal-proximal depth of cut D2 of the anterior cut 107.

The distance L1 may be additionally or alternatively considered with reference to FIG. 6B. As shown, the anterior slot 114 extends along a first axis through the guide 102 parallel to the anterior-posterior direction A-P, and parallel to an anterior-posterior reference plane A-P-R-P. The distal stop element 128 extends along a second axis toward the surface of the patellar groove of the femur 18, substantially parallel to the distal-proximal direction D-P and transverse (preferably orthogonal) to the anterior-posterior reference plane A-P-R-P. An orthogonal distance from the anterior-posterior reference plane A-P-R-P to the anterior slot 114 is L2. An orthogonal distance from the anterior-posterior reference plane A-P-R-P to the terminal end of the distal stop element 128 is L3. The difference between L2 and L3 is L1, the distal-proximal depth of cut D2 of the anterior cut 107.

In order to ensure that the distal-proximal depth of cut D2 of the anterior cut 107 is of suitable uniformity, or at least exhibits suitable characteristics to accommodate the prosthesis 10, the anterior slot 114 preferably lies in a plane that is parallel to the anterior-posterior direction A-P, and the distal-proximal direction D-P is orthogonal to such plane. Otherwise, the depth of cut of the anterior cut 107 would vary significantly as one traversed in the medial-laterally direction.

Although aspects of the invention are not limited by any particular theory of operation, it has been found that desirable characteristics of the modified femur 18 are achieved when the distal-proximal depth of cut D2 of the anterior cut 107 is in the range of 1.0 to 8.0 mm.

The cutting edge 106A of the distal punch 104 defines a V-shaped edge (and thus a V-shaped anterior cut 107), when viewed in the distal-proximal direction D-P. Preferably, the V-shaped edge includes a rounded inflection region 106C. It is noted that the V-shaped edge and cut 106 are again sized and shaped to complement the shape and contour of the distal member 20 of the prosthesis 10, specifically the a generally V-shaped peripheral edge 22 (which also may include the rounded inflection region 24).

Figure 9B:
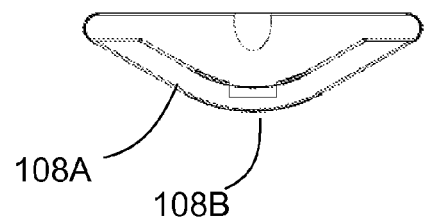
FIGS. 9A and 9B are a respective perspective view of a trochlear punch referenced to the patient's femur, and an end view of the punch, which punch may be utilized with the system of FIG. 5.
Figure 9A:
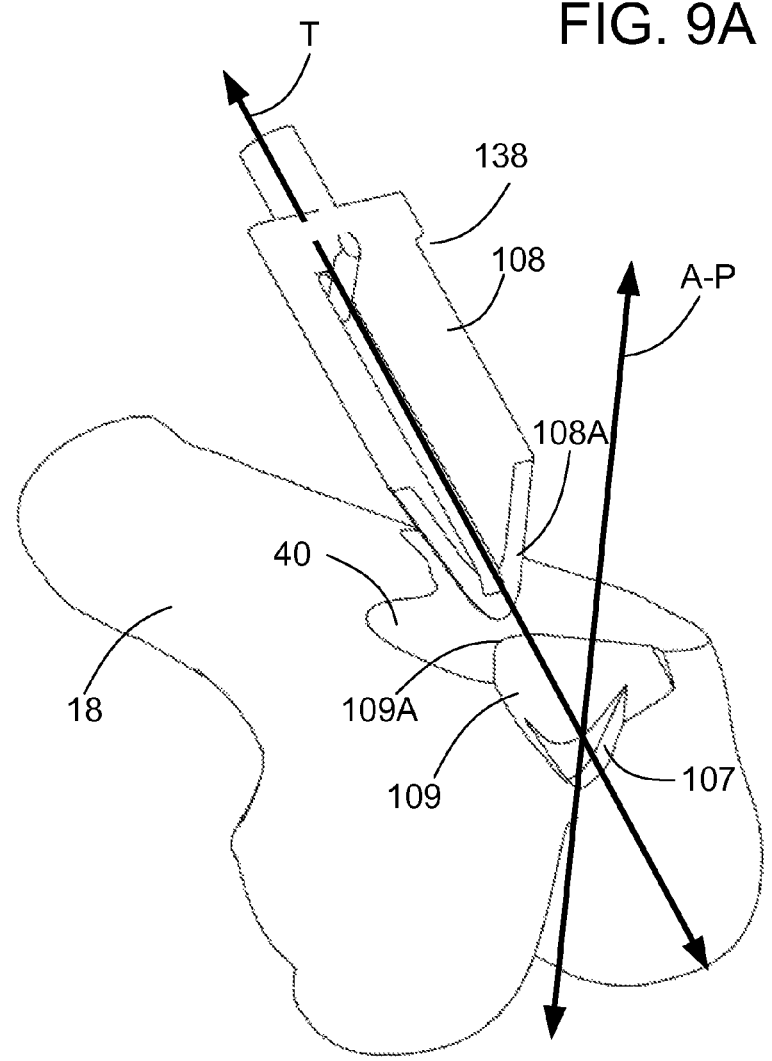

With reference to FIGS. 5 and 9A-9B, the trochlear punch 108 includes a cutting edge 108A, and is sized and shaped to slidingly pass through the transverse slot 112 such that the cutting edge 108A penetrates through the anterior resection surface 40 and through the anterior cut 107, thereby forming a trochlear cut 109 in both anterior and distal portions of the femur 18. The trochlear cut 109 is of generally concave cross-section (or grooved as the name implies) in order to complement the convex rear surface 30 of the distal member 20 of the prosthesis 10. A most proximal edge 109A of the trochlear cut 109 complements the edge 32 of the prosthesis 10 that extends along a transitional region between the convex rear surface 30 and the further rear surface 36 (opposite the surface 14) of the prosthesis 10. Thus, both the proximal edge 109A and the transitional edge 32 are of compound V-shape, including matching rounded inflection regions.

As one skilled in the art will appreciate from the discussion herein, a depth (compound depth from the anterior and distal directions) and orientation of the trochlear cut 109 are important in order to ensure that the prosthesis 10 fits properly into the cavity thereby formed in the femur 18.

The trochlear punch 108 and the guide 102 (or frame thereof) includes a depth limiting element operating to limit the sliding of the trochlear punch 108 through the proximal slot 112. By way of example, the punch 108 may include a collar 138 located proximate to a hub of the punch (which is the transition to a handle thereof, not shown). The collar 138 operates to engage a stop member located at a periphery of the slot 112. In such a configuration, a distance through which the punch 108 slides through the slot 112 is limited.

Such limiting, however, is not as critical as the location and angle of the transverse direction T, which significantly affects the contours and peripheral shape and size of the resulting trochlear cut 109. Indeed, if the intersection of the transverse direction T and the anterior-posterior direction A-P were further to the posterior, then the compound depth of the trochlear cut 109 would increase (removing more material from the femur 18). Conversely, if the intersection of the transverse direction T and the anterior-posterior direction A-P were further to the anterior, then the compound depth of the trochlear cut 109 would decrease (removing less material from the femur 18). A precise, repeatable and accurate depth of cut is obtained, however, using the guide 102 as discussed above. Similarly, varying the angle, a2, of the transverse direction T will modify the depths of the trochlear cut 109 in the anterior and posterior areas of the femur 18.

As with the distal punch 104, the cutting edge 108A of the trochlear punch 108 defines a V-shaped edge (and thus a V-shaped trochlear cut 109), when viewed in the transverse direction T. Preferably, the V-shaped edge includes a rounded inflection region 108B. It is noted that the V-shaped edge and cut 109 are sized and shaped to complement the shape and contour of the rear surface 30 of the distal member 20 of the prosthesis 10.

Alternatively or additionally, the depth limiting features discussed above may include some indicia located on one or more of the punches 104, 106, 108 (such as a line or other marking), which with reference to one or more structures of the guide 102 or the femur 18, provides a respective visual indication as to a desired depth to which to drive the respective punch into the femur 18.

Reference is again made to the system 100A of FIG. 3. Those skilled in the art will appreciate that aspects of the invention are directed to the punches 104, 106, 108 alone (without the guide 102, or any guide) and/or to the punches 104, 106, 108 in combination with alternative guides, differing from the guide 102 shown and described herein by way of example. The system 100A is intended to apply defined orientations for the punches 104, 106, 108 to remove material from the femur 18 and to create the cuts 105, 107, 109 (including all the desired depths, shapes, etc. described above) to accommodate the distal member 20 of the prosthesis 10.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. An apparatus for modifying a patient's femur for receiving a patellofemoral prosthesis, comprising:
   a guide operating to engage a distal end of the femur, the guide including: (i) a mounting element disposed at a first end of the guide, having an engagement surface defining an anterior resection plane, and operating to rigidly couple the guide to an anterior resection surface of the femur, (ii) a distal slot extending through the guide, toward a patellar groove of the femur in a distal-proximal direction when the guide is coupled to the anterior resection surface of the femur, and (iii) an anterior slot extending through the guide, transverse to the anterior resection plane, toward the patellar groove of the femur in an anterior-posterior direction when the guide is coupled to the anterior resection surface of the femur;
   a distal punch having a cutting edge and being sized and shaped to slidingly pass through the distal slot such that the cutting edge of the distal punch penetrates into the patellar groove of the femur, in the distal-proximal direction, producing a distal cut;
   an anterior punch having a cutting edge and being sized and shaped to slidingly pass through the anterior slot such that the cutting edge of the anterior punch penetrates into the patellar groove of the femur, in the anterior-posterior direction, producing an anterior cut, wherein the respective cutting edges of the distal punch and the anterior punch are sized and shaped, and wherein the respective distal and anterior slots are oriented, such that the anterior cut meets the distal cut and a portion of the patient's femur is removed to receive a portion of the patellofemoral prosthesis; and
   a trochlear punch having a cutting edge and being sized and shaped to slidingly pass through a transverse slot extending through the guide such that the cutting edge of the trochlear punch penetrates through the anterior resection surface and through the anterior cut, thereby forming a trochlear cut in both anterior and distal portions of the femur.

2. The apparatus of claim 1, further comprising: a distal stop element extending from a second, opposite end of the guide, and operating to engage a surface of the patellar groove of the femur, thereby establishing a position at which the mounting element couples the guide to the anterior resection surface of the femur, and establishing orientations of the distal and anterior slots with respect to the patellar groove of the femur.

3. The apparatus of claim 2, wherein the guide includes a frame, the frame comprising: an anterior section extending away from the first end of the guide along an axis substantially parallel to the distal-proximal direction, the anterior slot extending through the anterior section of the frame, transverse to the anterior resection plane, toward the patellar groove of the femur in the anterior-posterior direction when the guide is coupled to the anterior resection surface of the femur;
   a distal section extending transversely away from the anterior section along an axis substantially parallel to the anterior-posterior direction, the distal slot extending through the distal section of the frame, toward the patellar groove of the femur in the distal-proximal direction when the guide is coupled to the anterior resection surface of the femur, wherein the distal stop element extends from the distal section of the frame, along an axis substantially parallel to the distal-proximal direction, to engage the surface of the patellar groove of the femur, thereby establishing the orientations of the distal and anterior slots with respect to the patellar groove of the femur.

4. The apparatus of claim 2, wherein the guide includes a frame, and at least one of the distal punch and the frame include a depth limiting element operating to limit the sliding of the distal punch through the distal slot such that the cutting edge of the distal punch may extend only a predetermined length past the distal stop element, in the distal-proximal direction, thereby defining a depth of the distal cut.

5. The apparatus of claim 4, wherein the depth limiting element operates such that the depth of the distal cut is in the range of about 1.0 to 8.0 mm.

6. The apparatus of claim 2, wherein the cutting edge of the distal punch defines the distal cut having one of:
   (i) a V-shape when viewed in the distal-proximal direction; and
   (ii) a V-shape that includes a rounded inflection region when viewed in the distal-proximal direction.

7. The apparatus of claim 2, wherein a distance, L1, between a terminal end of the distal stop element and the anterior slot, along an axis substantially parallel to the distal-proximal direction establishes a distal-proximal depth D2 of the anterior cut.

8. The apparatus of claim 7, wherein:
   the anterior slot extends along a first axis through the guide parallel to the anterior-posterior direction, and parallel to an anterior-posterior reference plane;
   the distal stop element extends along a second axis toward the surface of the patellar groove of the femur when engaging a surface of the patellar groove of the femur, transverse to the anterior-posterior reference plane; and
   respective orthogonal distances between: (i) the anterior slot and the anterior-posterior reference plane, and (ii) the terminal end of the distal stop element and the anterior-posterior reference plane, differ by the distance L1, thereby establishing the distal-proximal depth D2 of the anterior cut.

9. The apparatus of claim 8, wherein the distance L1 is such that the distal-proximal depth D2 of the anterior cut is in a range of 1.0 to 8.0 mm.

10. The apparatus of claim 1, wherein the guide includes a frame, and at least one of the anterior punch and the frame include a depth limiting element operating to limit the sliding of the anterior punch through the anterior slot such that the cutting edge of the anterior punch may extend only a predetermined length into the femur, in the anterior-posterior direction, thereby defining an anterior-posterior depth, D1, of the anterior cut.

11. The apparatus of claim 1, wherein the cutting edge of the anterior punch defines the anterior cut having one of:
   (i) a V-shape when viewed in the distal-proximal direction; and
   (ii) a V-shape that includes a rounded inflection region when viewed in the distal-proximal direction.

12. The apparatus of claim 1, wherein the anterior-posterior direction and the distal-proximal direction are orthogonal to one another.

13. The apparatus of claim 12, wherein:
   the anterior slot lies in a plane that is parallel to the anterior-posterior direction; and
   the distal-proximal direction is orthogonal to the plane of the anterior slot.

14. The apparatus of claim 1, wherein the cutting edge of the distal punch has a V-shape and the cutting edge of the anterior punch has a V-shape.

15. The apparatus of claim 1, wherein the distal punch, the anterior punch, and the trochlear punch are separate punches.

16. The apparatus of claim 1, wherein the distal punch and the anterior punch have different shapes.

17. An apparatus for modifying a patient's femur for receiving a patellofemoral prosthesis, comprising:
   a guide operating to engage a distal end of the femur, the guide including: (i) a mounting element disposed at a first end of the guide, having an engagement surface defining an anterior resection plane, and operating to rigidly couple the guide to an anterior resection surface of the femur, (ii) a distal slot extending through the guide, toward a patellar groove of the femur in a distal-proximal direction when the guide is coupled to the anterior resection surface of the femur, and (iii) an anterior slot extending through the guide, transverse to the anterior resection plane, toward the patellar groove of the femur in an anterior-posterior direction when the guide is coupled to the anterior resection surface of the femur, and the guide includes a transverse slot extending through the guide in a transverse direction, which is transverse to:
   i) the anterior resection plane
   ii) the distal-proximal direction, and
   iii) the anterior-posterior direction, when the guide is coupled to the anterior resection surface of the femur;
   a distal punch having a cutting edge and being sized and shaped to slidingly pass through the distal slot such that the cutting edge of the distal punch penetrates into the patellar groove of the femur, in the distal-proximal direction, producing a distal cut;
   an anterior punch having a cutting edge and being sized and shaped to slidingly pass through the anterior slot such that the cutting edge of the anterior punch penetrates into the patellar groove of the femur, in the anterior-posterior direction, producing an anterior cut, wherein the respective cutting edges of the distal punch and the anterior punch are sized and shaped, and wherein the respective distal and anterior slots are oriented, such that the anterior cut meets the distal cut and a portion of the patient's femur is removed to receive a portion of the patellofemoral prosthesis; and
   a trochlear punch having a cutting edge and being sized and shaped to slidingly pass through the transverse slot such that the cutting edge of the trochlear punch penetrates through the anterior resection surface and through the anterior cut, thereby forming a trochlear cut in both anterior and distal portions of the femur.

18. The apparatus of claim 17, wherein at least one of:
   the transverse direction extends about 15-45° with respect to at least one of the anterior resection plane and the distal-proximal direction; and
   the transverse direction extends about 30° with respect to at least one of the anterior resection plane and the distal-proximal direction.

19. The apparatus of claim 17, wherein the guide includes a frame, the frame comprising:
   a proximal section extending away from the mounting element of the guide, the transverse slot extending through the proximal section of the frame, in the transverse direction when the guide is coupled to the anterior resection surface of the femur;
   an anterior section extending away from the first end of the guide along an axis substantially parallel to the distal-proximal direction, the anterior slot extending through the anterior section of the frame, transverse to the anterior resection plane, toward the patellar groove of the femur in the anterior-posterior direction when the guide is coupled to the anterior resection surface of the femur;
   a distal section extending transversely away from the anterior section along an axis substantially parallel to the anterior-posterior direction, the distal slot extending through the distal section of the frame, toward the patellar groove of the femur in the distal-proximal direction when the guide is coupled to the anterior resection surface of the femur, wherein a distal stop element extends from the distal section of the frame, along an axis substantially parallel to the distal-proximal direction, to engage a surface of the patellar groove of the femur, thereby establishing orientations of the transverse, distal and anterior slots with respect to the anterior and distal portions of the femur.

20. The apparatus of claim 19, wherein at least one of:

the anterior section of the frame extends transversely with respect to both the proximal and distal sections of the frame;

at least two of the proximal, anterior and distal sections of the frame extend orthogonally with respect to one another;

the anterior and distal sections of the frame extend orthogonally with respect to one another;

the proximal, anterior, and distal sections of the frame extend transversely with respect to one another; and the proximal and distal sections of the frame extend at an angle of at least one of: about 2-8° with respect to one another, about 4-6° with respect to one another, and about 5° with respect to one another.

21. The apparatus of claim 17, wherein the cutting edge of the trochlear punch defines the trochlear cut having one of:
   (i) a V-shape when viewed in the transverse direction; and
   (ii) a V-shape that includes a rounded inflection region when viewed in the transverse direction.

22. The apparatus of claim 17, wherein the cutting edge of the distal punch has a V-shape and the cutting edge of the anterior punch has a V-shape.

23. The apparatus of claim 17, wherein the distal punch, the anterior punch, and the trochlear punch are separate punches.

24. The apparatus of claim 17, wherein the distal punch and the anterior punch have different shapes.

* * * * *